United States Patent [19]
Moore

[11] Patent Number: 5,798,075
[45] Date of Patent: Aug. 25, 1998

[54] ADJUSTMENT OF MOSAIC SPREAD FOR HIGHLY ORIENTED PYROLYTIC GRAPHITE

[75] Inventor: Arthur William Moore, Strongsville, Ohio

[73] Assignee: Advanced Ceramics Corporation

[21] Appl. No.: 728,933

[22] Filed: Oct. 11, 1996

[51] Int. Cl.$^6$ ............................................. B29C 43/00
[52] U.S. Cl. .................... 264/320; 264/40.1; 264/81
[58] Field of Search .................... 264/320, 29.1, 264/81, 40.1

[56] References Cited

U.S. PATENT DOCUMENTS 5,552,008  9/1996  Hecht ............................ 264/29.6

FOREIGN PATENT DOCUMENTS 48-29610  9/1973  Japan ............................ 264/320

Primary Examiner—James Derrington
Attorney, Agent, or Firm—Eugene Lieberstein; Michael N. Meller

[57] ABSTRACT

This invention is directed to a method for shifting the mosaic spread of highly oriented pyrolytic graphite ("HOPG") into a preselected narrow range. The method involves selecting HOPG samples having a mosaic spread which lies below a desired mosaic spread range and cold working the selected samples to form a textured surface sufficent to shift the mosaic spread of the samples into the desired mosaic spread range. The textured surface is preferably imprinted by pressing the samples between metal dies with at least one of the dies having a knurled surface.

11 Claims, 3 Drawing Sheets

SYSTEM FOR ROOM TEMPERATURE PRESSING OF HOPG BETWEEN METAL DIES WITH KNURLED SURFACES.

GROOVES ENLARGED 10-20X TO ILLUSTRATE SHAPE.
GROOVES ARE CRISS-CROSSED, I.E., THERE IS ANOTHER SET OF GROOVES MACHINED AT 90° TO THOSE SHOWN IN THE FIGURE.

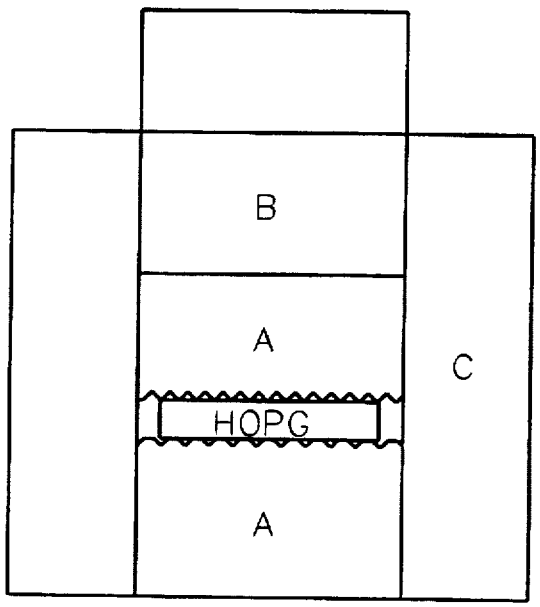

FIG. 2

SYSTEM FOR ROOM TEMPERATURE PRESSING OF HOPG BETWEEN METAL DIES WITH KNURLED SURFACES.

GROOVES ENLARGED 10-20X TO ILLUSTRATE SHAPE.
GROOVES ARE CRISS-CROSSED, I.E., THERE IS ANOTHER SET OF GROOVES MACHINED AT 90° TO THOSE SHOWN IN THE FIGURE.

FIG. 3

SYSTEM FOR PRESSING HOPG BETWEEN A METAL DIE WITH A KNURLED SURFACE AND ONE WITH A SMOOTH SURFACE ON WHICH IS MOUNTED A PAPER PAD.

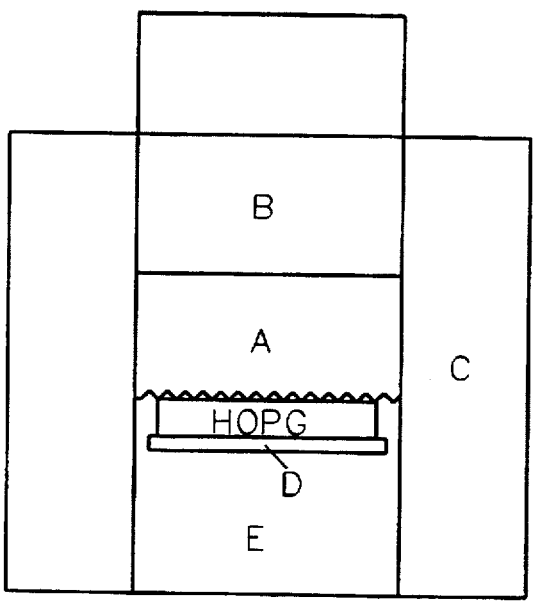

LEGEND:

(A) STEEL OR BRASS DIE WITH KNURLED SURFACE
(B) PISTON
(C) CYLINDER
(D) PAPER PAD
(E) METAL DIE WITH SMOOTH SURFACE

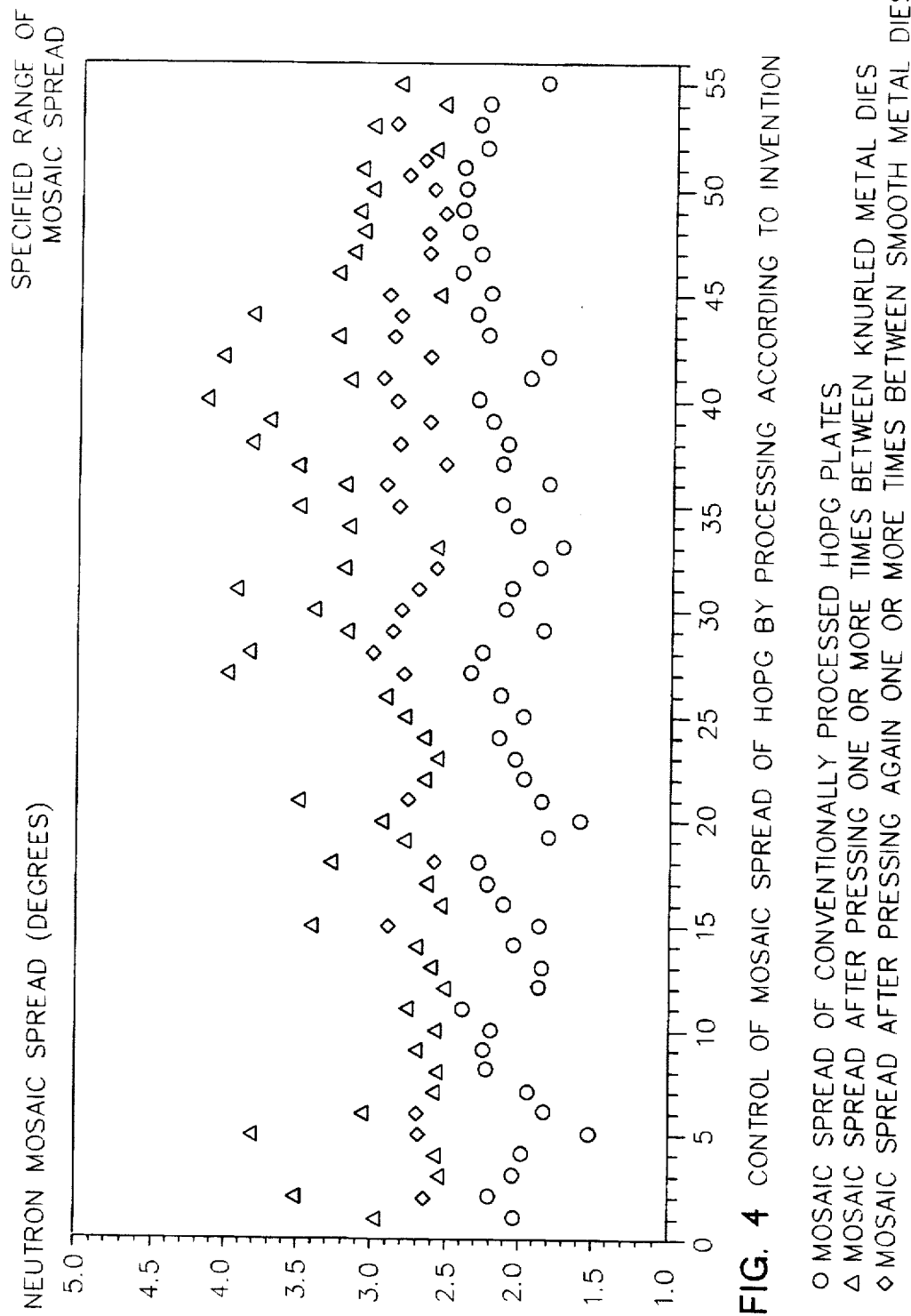

5,798,075

1

ADJUSTMENT OF MOSAIC SPREAD FOR HIGHLY ORIENTED PYROLYTIC GRAPHITE

FIELD OF THE INVENTION

This invention relates to a method for shifting the mosaic spread of highly

BACKGROUND OF THE INVENTION

Graphite monochromaters are highly oriented forms of high purity pyrolytic graphite which diffract x-rays and neutrons to generate a monochromatic beam of x-rays and/or neutrons for use in a spectrometer for measuring the characteristics of crystalline materials.

Graphite monochromaters are classified according to their mosaic spread characteristic. The mosaic spread is a measurement of the full width at half maximum intensity of the reflection of an x-ray beam from a sample of HOPG material when tilted in a preferred orientation thereby forming a preferred orientation x-ray diffraction curve known as a "rocking curve". The rocking curve is a graph of the intensity of the reflected x-rays as a function of the angular distance from a reference plane using Bragg's Law to determine the angular deviation. The rocking curve is determined for each HOPG sample so that its mosaic spread can be categorized into different standard mosaic spread ranges.

When a customer desires to purchase an HOPG monochromater the selection is made from standard grades corresponding to the different mosaic spread ranges. One production grade of HOPG material has a wide mosaic spread range of 3.5°±1.50°. However, a customer may request a particular HOPG grade material having a narrower range of mosaic spread of e.g. (±0.25°). To satisfy this request at present would adversely affect the yield from conventionally processed HOPG material. For the above example only about 30% of the HOPG material made by conventional processing would meet the narrower mosaic spread specification of ±0.25°.

SUMMARY OF THE INVENTION

The method of the present invention can assure a yield of up to 100% of HOPG material having a mosaic spread tailored to any desired preselected narrow range starting from HOPG processed material having a mosaic spread below the desired final mosaic spread specification for the material.

The method of the present invention comprises the steps of selecting HOPG samples of material having a mosaic spread which lies below a desired mosaic spread range and cold working the selected samples to imprint a surface texture sufficent to shift the mosaic spread of the samples into the desired mosaic spread range. The textured surface is preferably imprinted by pressing the samples between metal dies with at least one of the dies having a knurled surface.

BRIEF DESCRIPTION OF THE DRAWINGS

The advantages of the present invention will become apparent from the following detailed description of the present invention when read in conjunction with the accompanying drawings of which:

FIG. 2 is a diagrammatic illustration of an arrangement of metal dies for cold working the HOPG samples in accordance with the present invention;

2

Figure 1:
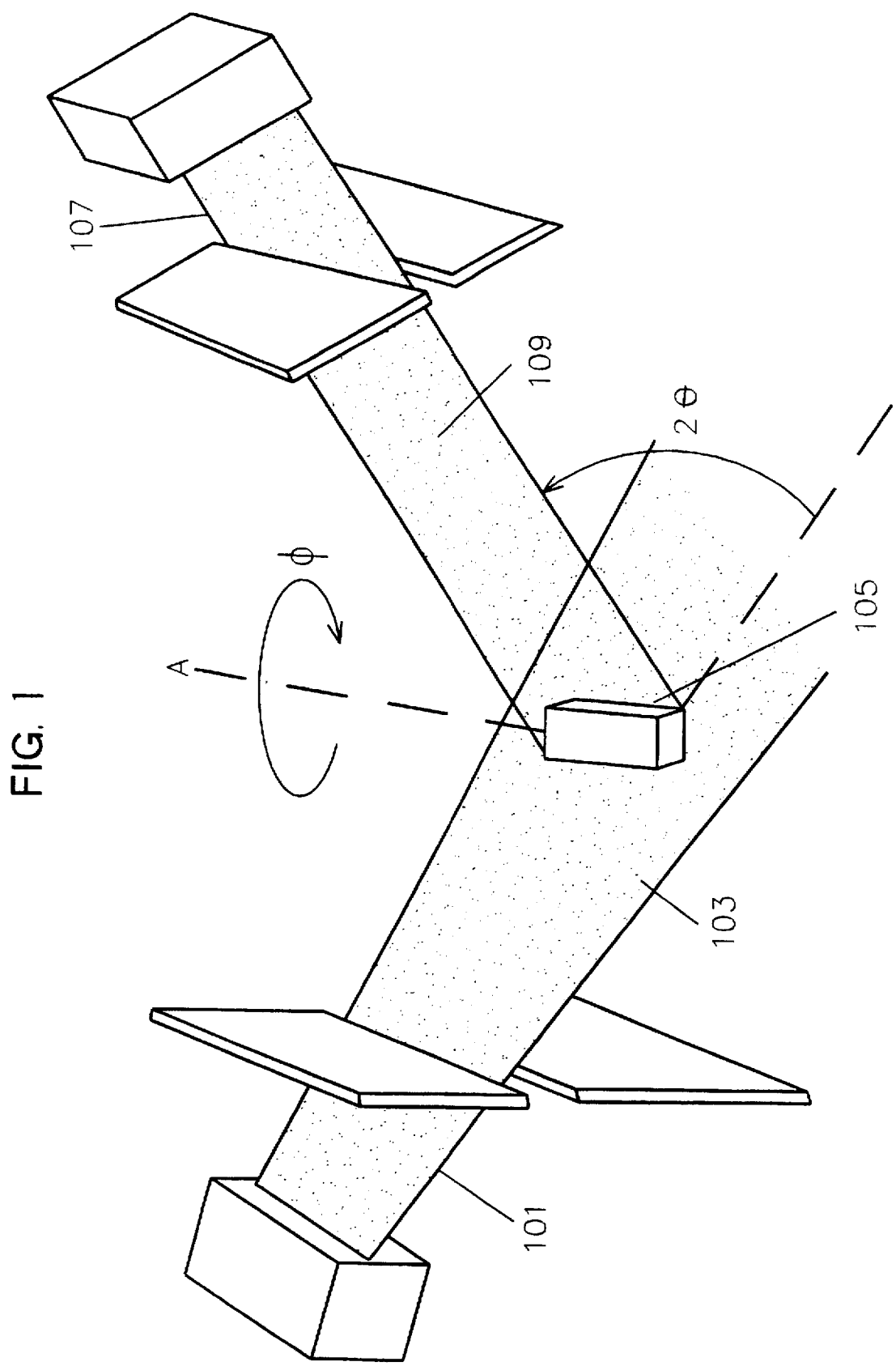
FIG. 1 is a simplified perspective view of an apparatus for producing a rocking curve for the HOPG samples to establish its mosaic spread.

FIG. 3 is another embodiment of an arrangement similar to FIG. 2 for cold working the HOPG samples in accordance with the present invention; and FIG. 4 is a graph illustrating the principles of the present invention for adjusting the mosaic spread to within any desired range above the mosaic spread level before adjustment.

DETAILED DESCRIPTION OF THE INVENTION

Graphite is made up of layer planes of hexagonal arrays or networks of carbon atoms. These layer planes of hexagonal arranged carbon atoms are substantially flat and are oriented so as to be substantially parallel and equidistant to one another. The substantially flat parallel layers of carbon atoms are referred to as basal planes and are linked or bonded together in groups arranged in crystallites. Conventional or electrolytic graphite has a random order to the crystallites. Highly ordered graphite has a high degree of preferred crystallite orientation. Accordingly, graphite may be characterized as laminated structures of carbon atoms having two principal axes, to wit, the "c" axes which is generally identified as the axes or direction perpendicular to the carbon layers and the "a" axes or direction parallel to the carbon layers and transverse to the c axes. Graphite materials which exhibit a high degree of orientation include natural graphite and synthetic or pyrolytic graphite. Pyrolytic graphite is produced by the pyrolysis of a carbonaceous gas on a suitable substrate at elevated temperature. Briefly, the pyrolytic deposition process may be carried out in a heated furnace heated to above 1500 °C. and up to 2500°C. and at a suitable pressure, wherein a hydrocarbon gas such as methane, natural gas, acetylene etc. is introduced into the heated furnace and is thermally decomposed at the surface of a substrate of suitable composition such as graphite having any desirable shape. The substrate may be removed or separated from the pyrolytic graphite. The pyrolytic graphite may then be further subjected to thermal annealing at high temperatures to form a highly oriented pyrolytic graphite commonly referred to as "HOPG" or "TPG" material. "Highly oriented pyrolytic graphite" (HOPG) for purposes of the present invention shall mean pyrolytic graphite which has been annealed at high temperature of substantially equal to or above 3000°C. The HOPG samples are conventionally produced as flat plates or in singly-bent and doubly-bent shapes.

The structure and preferred orientation of the HOPG plate samples are determined by x-ray diffraction. FIG. 1 shows an arrangement for producing a rocking curve. An x-ray source 101 with a low source divergence angle, typically 1° or less directs a monochromatic x-ray beam 103 upon a sample 105. A detector 107 is placed at the 2θ position to detect the reflected x-ray beam 109 from the sample. The reflected beam 109 shows peak intensities at sample angles (Φ) corresponding to the Bragg (002) reflections from the basal planes of the crystal lattice of the sample. The angle 2θ at which the x-ray beam is reflected is calculated using Bragg's Law ($\lambda = 2d \uparrow \sin \theta$), where $\lambda$ is the wavelength of the monochromatic x-ray beam, d is the interlayer spacing of the crystal and θ is the Bragg angle. In the present application the x-rays were generated with a CuKα (1.54 Å wavelength) x-ray source. The sample 105 is rotated about axis A—A within the beam 103. As the sample 105 is rotated the x-ray intensity is detected, including the intensity peak corresponding to the Bragg reflection at the 002 basal plane thereby forming a rocking curve of reflected x-ray intensity vs. angle (θ) of rotation of the sample. The rocking curve is a graph of the intensity of the reflected x-rays as a function of the angular distance from a reference plane, which in the case of pyrolytic graphite is the deposition plane. Therefore a peak at 0° indicates a (002) basal plane parallel to the deposition plane defined by the substrate. The "FWHM" of a peak on the rocking curve is the Full width of a peak at one-half of the maximum intensity of the peak. FWHM is a measure of the degree of the preferred orientation of the 002 plane, the highly oriented crystal structure producing a smaller FWHM (narrow peak) and a poorly oriented crystal structure producing a larger FWHM (broad peak). The mosaic spread is a measurement in degrees of the FWHM (full width at half maximum) intensity of the reflection of the x-ray beam from the HOPG samples an d varies due to variations from sample to sample and from variations in conditions in the furnace.

Highly oriented pyrolytic graphite (HOPG) with a mosaic spread of 3.5°±1.5° is used extensively as a filter for higher order neutrons in neutron spectrometry. In accordance with this invention the mosaic spread of conventionally produced HOPG having a mosaic spread below a desired range can be increased to fall within the desired range by cold working of the samples at room temperature.

One embodiment for practicing the present invention is shown in FIG. 2 and includes a cylinder 12 and two knurled metal dies 13 and 14 respectively. A sample piece of HOPG 10 with a lower than desired mosaic spread is placed between the dies 13 and 14 inside the cylinder 12 and subjected to a pressure of up to 5000 psi using a hydraulic press. After 5–30 seconds at this pressure, the pressure is released and the HOPG is removed. For best results, the knurled surfaces 15 and 16 of the dies 13 and 14 are keyed together along the cylinder 12 so that the surface protrusions on one die match the valleys on the other die i.e., the knurled surfaces interdigitate preferably with "criss-cross" grooves. The dimensions of the knurled surfaces 15 and 16 with the grooves 18 and 19 shown enlarged by 10–20× in FIGS. 2 and 3 are preferably between 0.005–0.010 inch deep by 0.015–0.030 inch apart. Brass and stainless steel dies may be used although steel dies are preferred for better wear resistance.

FIG. 3 is a variation of the embodiment of FIG. 2. Here the HOPG sample is pressed between one knurled die 20 and a pad 21 of deformable material (such as paper 0.010–0.020 inch thick) mounted on a smooth flat die 22. This method also achieves the desired texturing throughout the thickness of the HOPG which increases the mosaic spread. With this system, the knurled die 20 does not have to be keyed to the cylinder 12 because no specific orientation with respect to the flat die 22 is needed.

The mosaic spread of the HOPG is measured after being pressed against the knurled dies 3 and 14. If the mosaic spread is too high, the HOPG is placed between smooth flat dies (not shown) and pressed again, usually at a lower pressure than that applied using the knurled dies, but in a preferred range of 500–5000 psi. In some cases repeated pressings between knurled dies and smooth dies may be required to bring the mosaic spread into a tight (very narrow) specification range.

FIG. 4 shows 55 examples illustrating the invention. Each sample piece of HOPG was 34.5×27.1×1.5 mm thick. The neutron mosaic spread of these conventionally processed pieces was 1.52–2.34°. Assume a desired neutron mosaic spread of 2.50–3.00°. This is shown obtained on 25 of these pieces by pressing one or more times using the knurled dies. The mosaic spread of the other 30 pieces is shown as lying between 3.03–4.13° after pressing between knurled dies. The mosaic spread of these 30 pieces was then decreased to 2.50–3.00° by pressing them one or more times between smooth flat dies. Since the mosaic spread can be readily increased by pressing between knurled dies, and decreased again by pressing between smooth dies, it is clear that still smaller variations in mosaic spread, such as ±0.05°, can be achieved by multiple pressings.

The following specific examples were taken from FIG. 4 to further explain and illustrate the invention. For each example, the following conditions are constant. The HOPG pieces are all 34.5×27.1×1.5 mm thick. The brass and steel dies are 2-inch diameter. The neutron mosaic spread of the HOPG (002) reflection was measured on the SPINS instrument of neutron guide 5 at 4.15 Å at N.I.S.T., Gaithersburg, Md.

Example 1 (Piece 1)

A piece of HOPG with initial neutron mosaic spread of 2.04° was pressed between knurled stainless steel dies with crisscrossed grooves 0.005 inch deep and 0.015 inch apart at 5000 psi for 15 seconds. After this pressing, the neutron mosaic spread of the HOPG was 2.97°.

Example 2 (Piece 2)

A piece of HOPG with initial neutron mosaic spread of 2.24° was pressed between knurled brass dies with criss-crossed grooves 0.010 inch deep and 0.030 inch apart at 5000 psi for 15 seconds. After this pressing, the neutron mosaic spread of the HOPG sample was 3.520, above the desired range of 2.50–3.00°. The HOPG sample was pressed again between smooth brass dies at 2500 psi for 15 seconds. This operation reduced the mosaic spread of the HOPG to 2.640.

Example 3 (Piece 3)

A piece of HOPG with initial neutron mosaic spread of 2.03° was pressed between knurled brass dies with criss-crossed grooves 0.010 inch deep and 0.030 inch apart at 5000 psi for 15 seconds. The pressed HOPG was examined and pressed again at 5000 psi for 15 seconds. After the two pressings, the neutron mosaic spread of the HOPG was 2.52°.

Example 4 (Piece 18)

A piece of HOPG with initial neutron mosaic spread of 2.21° was pressed between one knurled brass die with crisscrossed grooves 0.010 inch deep and 0.030 inch apart and a smooth brass die on which was mounted a 0.015 inch thick pad of paper. Pressure was held at 5000 psi for 15 seconds. The HOPG was examined and pressed again under the same conditions. The neutron mosaic spread after these two pressings was 3.19°. A third pressing, using flat brass dies at 2500 psi for 15 seconds, reduced the neutron mosaic spread to 2.57°.

Example 5 (Piece 35)

A piece of HOPG with initial neutron mosaic spread of 2.12° was pressed between knurled brass dies with criss-crossed grooves 0.010 inch deep and 0.030 inch apart at 5000 psi for 15 seconds. After this pressing, the neutron mosaic spread of the HOPG was 3.57°. The HOPG was then pressed at 2800 psi for 15 seconds between smooth flat brass dies. This operation reduced the mosaic spread to 3.14°. The HOPG was a smooth brass die on which was mounted a 0.015 inch thick pad of paper. Pressure subsequently pressed twice at 5000 psi and 15 seconds between smooth brass dies. The final neutron mosaic spread of the HOPG was 2.85°.

Example 6 (Piece 49)

A piece of HOPG with initial neutron mosaic spread of 2.31° was pressed between knurled stainless steel dies with criss-cross grooves 0.005 inch deep and 0.015 inch apart at 5000 psi for 15 seconds. After this pressing, the neutron mosaic spread of the HOPG was 3.11°. The HOPG was then pressed between smooth stainless steel dies at 3000 psi for 15 seconds. The final neutron mosaic spread of the HOPG sample was 2.60°.

What I claim is:

1. A method for shifting the mosaic spread of highly oriented pyrolytic graphite into a preselected mosaic spread range comprising the steps of: selecting highly oriented pyrolytic graphite samples having a mosaic spread which lies below said preselected mosaic spread range and cold working the selected samples to form a surface textured imprint sufficient to shift the mosaic spread of the cold worked samples into said preselected mosaic spread range.

2. A method as defined in claim 1 wherein said cold working is performed by compressing the samples between dies at least one of which has a knurled surface.

3. A method as defined in claim 2 wherein the other die comprises a pad of deformable material mounted on a smooth flat surface.

4. A method as defined in claim 3 wherein said deformable material is paper.

5. A method as defined in claim 2 wherein each of said dies has a knurled surface.

6. A method as defined in claim 5 wherein two metal dies are used to form the textured surface with the knurled surface of each die being disposed relative to the other so that they interdigitate.

7. A method as defined in claim 6 wherein said metal dies are composed of stainless steel with the knurled surface of each die forming grooves having cross sectional dimensions in the range of 0.005–010 inches deep and 0.015–0.030 inch apart.

8. A method as defined in claim 2 wherein the highly oriented pyrolytic graphite samples are compressed at a first relatively high pressure.

9. A method as defined in claim 8 wherein the mosaic spread of said samples are readjusted downwardly from the mosaic spread established by said first compression by further compression of said samples at a second pressure which is lower than said first pressure.

10. A method as defined in claim 9 wherein said further compression of said samples is performed between dies having flat smooth surfaces.

11. A method as defined in claim 10 wherein said dies for performing said second compression are composed of brass.

* * * * *